United States Patent [19]

Cornwell

[11] Patent Number: 5,339,959
[45] Date of Patent: Aug. 23, 1994

[54] DISPOSABLE MEDICAL WASTE BAG

[75] Inventor: James T. Cornwell, Cleveland, Tenn.

[73] Assignee: QCI, Inc., Crossett, Ark.

[21] Appl. No.: 981,548

[22] Filed: Nov. 25, 1992

Related U.S. Application Data

[63] Continuation-in-part of Ser. No. 844,177, Mar. 2, 1992, Pat. No. 5,203,458.

[51] Int. Cl.⁵ .................. B65D 33/01; B65D 85/00
[52] U.S. Cl. .................. 206/524.8; 206/438; 383/62; 383/100
[58] Field of Search ............. 206/524.8, 438; 383/62, 383/71, 100, 103, 70; 137/223

[56] References Cited

U.S. PATENT DOCUMENTS

| | | | |
|---|---|---|---|
| 2,913,030 | 11/1959 | Fisher | 206/524.8 X |
| 3,334,805 | 8/1967 | Halbach | 383/70 |
| 3,412,926 | 11/1968 | Bostwick | 383/62 |
| 3,593,767 | 7/1971 | Smith | 206/524.8 X |
| 4,066,167 | 1/1978 | Hanna et al. | 383/62 X |
| 4,906,108 | 3/1990 | Herrington et al. | 383/62 X |
| 4,973,171 | 11/1990 | Bullard | 383/71 X |
| 5,040,904 | 8/1991 | Cornwell | 383/71 |
| 5,111,838 | 5/1992 | Langston | 137/223 |
| 5,142,970 | 9/1992 | ErkenBrack | 383/100 X |
| 5,203,458 | 4/1993 | Cornwell | 206/524.8 |

FOREIGN PATENT DOCUMENTS 404189752  7/1992  Japan ................. 206/524.8

Primary Examiner—Bryon P. Gehman
Attorney, Agent, or Firm—Notaro & Michalos

[57] ABSTRACT

A disposable medical waste bag having layers of polyethylene film has an open top and a seal at the bottom of the bag. The bag is filled to a desired level with medical waste and is sealed by closing off the top of the bag by twisting. After the top of the bag has been twisted and a twist is formed, the twist is bent over on itself and an adhesive tape located at a location on the outside of the bag is used to tape the twist to itself, thereby thoroughly sealing the bag. A normally-closed valve is provided on the bag and is removably engagable with a coupler that is used in conjunction with the hose of a central vacuum system of a medical facility such as a hospital. After the bag has been sealed such as by taping, the central vacuum system vacuums or sucks out excess air sealed within the bag thereby substantially decreasing the size of the bag. The seal located at the bottom are sealed bars of thermosealable polymer material having a plurality of triangular air pockets extending between the bars.

18 Claims, 7 Drawing Sheets

DISPOSABLE MEDICAL WASTE BAG

CROSS REFERENCE TO RELATED APPLICATION

The present application is a continuation-in-part application of Ser. No. 07/844,177, filed on Mar. 2, 1992 entitled DISPOSABLE SURGICAL GARMENT CONTAINER, now U.S. Pat. No. 5,203,458.

FIELD AND BACKGROUND OF THE INVENTION

The present invention relates in general to the disposal of medical waste and, in particular, to a new and useful bag and method for the disposal of medical waste using the central in-house vacuum available in a medical facility or hospital.

Currently, medical waste, including surgical garments and other contaminated or infectious wastes, are received and stored in containers or bags at various medical facilities such as hospitals. Once the containers or bags are filled to a specified level with the medical waste, they are, in turn, taken to appropriate disposal sites. Prior to shipment, the bags are usually sealed at their openings for containing the waste. The sealing of a disposal bag causes air to be trapped inside the bag and results in a much larger holding area.

U.S. Pat. No. 5,040,904 issued to the present inventor, for an infectious/medical waste containment carrier provides that a flexible container is sealed with a tie cord above its top level. Although infectious medical waste is sealed within the container, the contents of the container include both waste and trapped air.

U.S. Pat. No. 4,670,227 for an apparatus and method of handling infectious waste material illustrates that the medical waste bags used for disposal consist of a sealed bag containing waste and trapped air.

When transported in bulk, the medical waste bags with trapped air result in a much greater demand for transportation space and, in turn, increase the cost of transporting the waste which has to be incurred by a medical facility such as a hospital.

SUMMARY OF THE INVENTION

The present invention is a disposable medical waste bag and method for disposing medical waste by using the in-house vacuum or central suction of a medical facility such as a hospital.

The present invention comprises a disposable medical waste bag made of a material appropriate for containing medical waste, such as a polyethylene bag. The bag has an open top and unique seal located across the bottom of the bag.

The present invention can be made of a coextruded polyethylene film that is composed of three separate layers. That is, an outer layer of linear low-density polyethylene, a sandwich layer of low-density polyethylene and an inside layer of low-density polyethylene. All three layers can be made from virgin materials, i.e., those materials having no diarylides or heavy metals. Such a composition ensures that when incinerated, the bag emits no harmful gases and therefore produces clean ash.

A strip of tape such as a self-adhesive polyethylene tape is attached on the outer layer of the bag and is removed from the bag by peeling when the bag is ready to be sealed for disposal. After the bag is filled to a desired level, the opening at the top of the bag is gathered up and twisted so that the bag is completely sealed, forming a twist extending from the top of the bag. The twist of excess bag material that has been twisted is, in turn, bent upon itself and fastened using the tape.

A normally-closed valve is provided on the bag so that the bag can be hooked up to the central vacuum or central suction of a medical facility. By engaging the normally-closed valve with a hospital's central suction system, excess air that is trapped within the bag is sucked out of the bag, thus creating a substantially smaller package containing medical waste.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
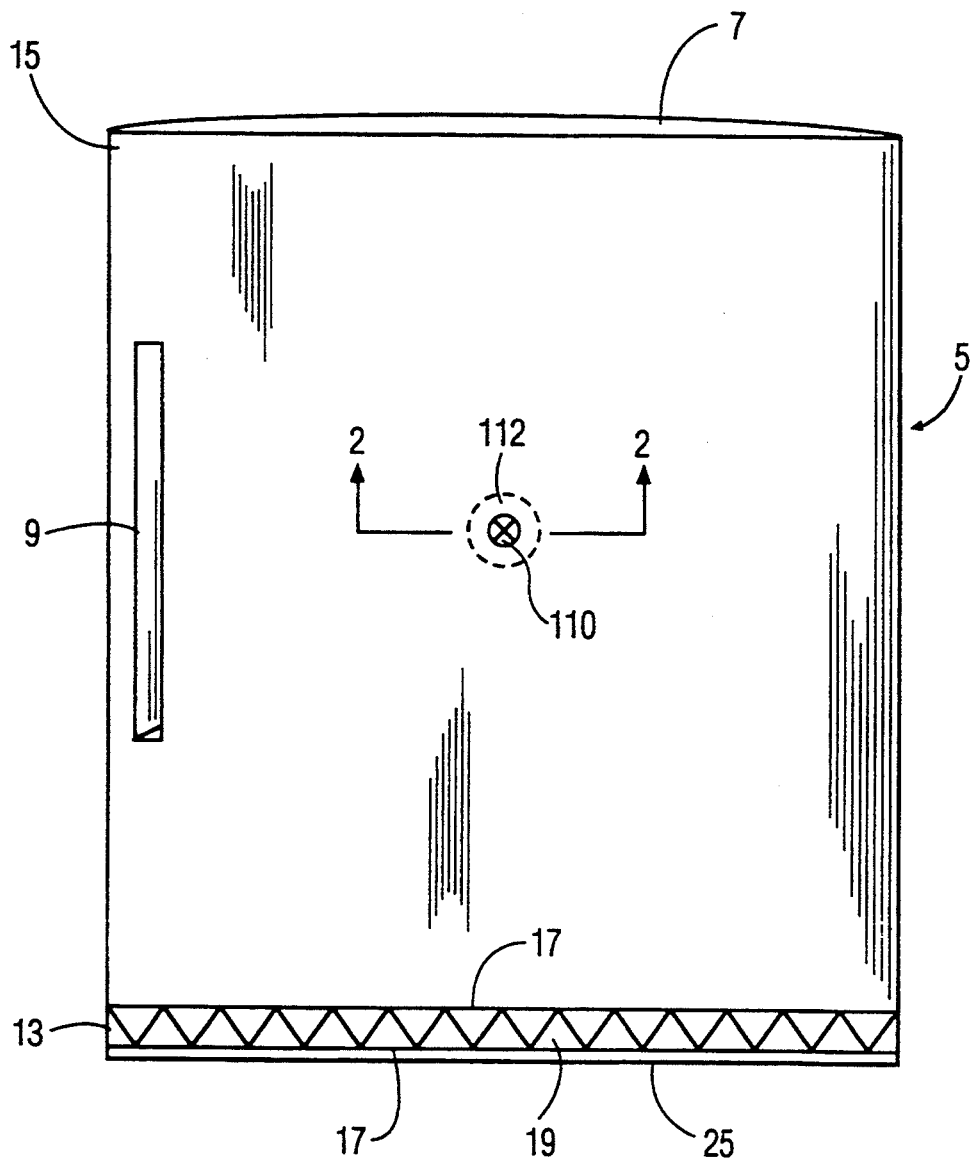
FIG. 1 is a perspective view of a medical waste bag according to the present invention.
Figure 3:
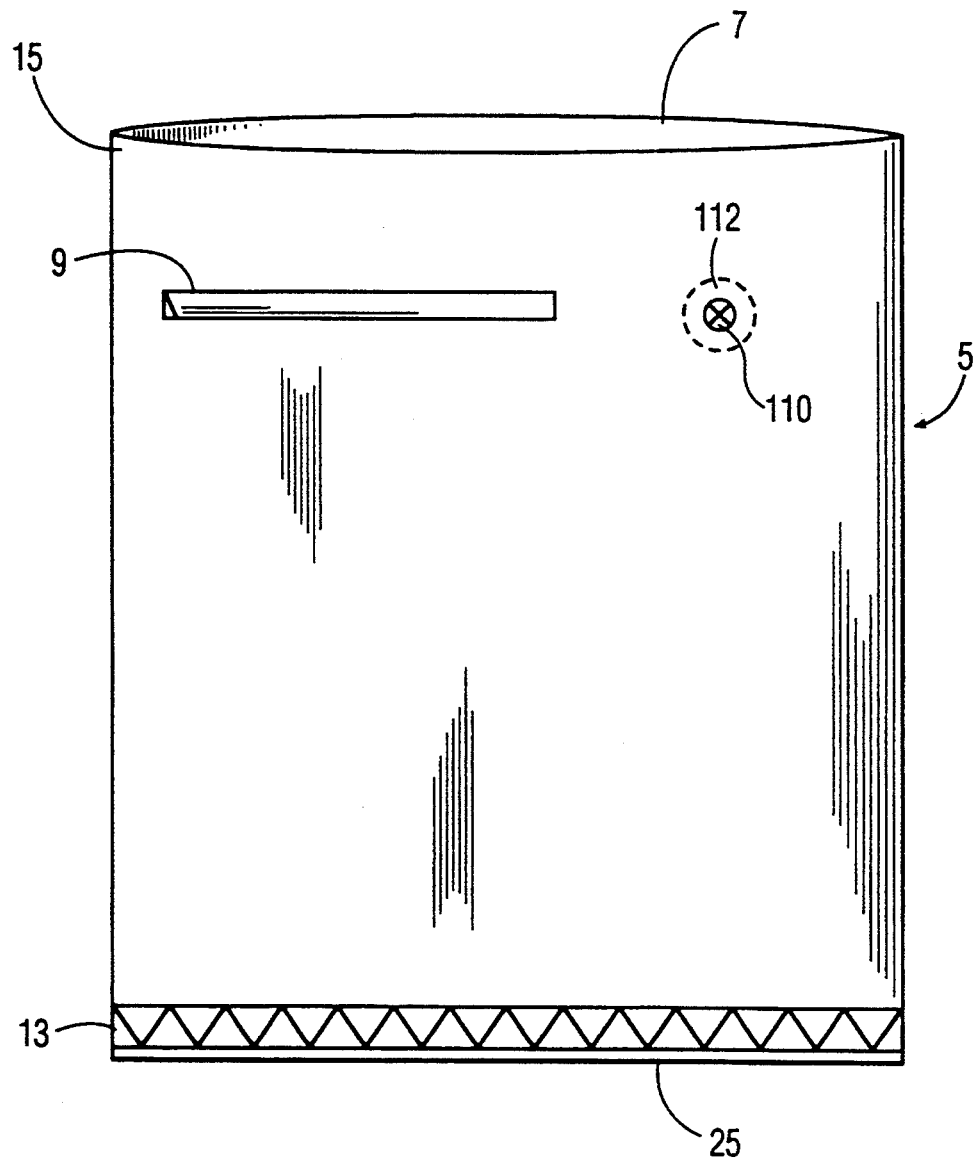
FIG. 3 is a perspective view of a second embodiment of the bag.
Figure 4:
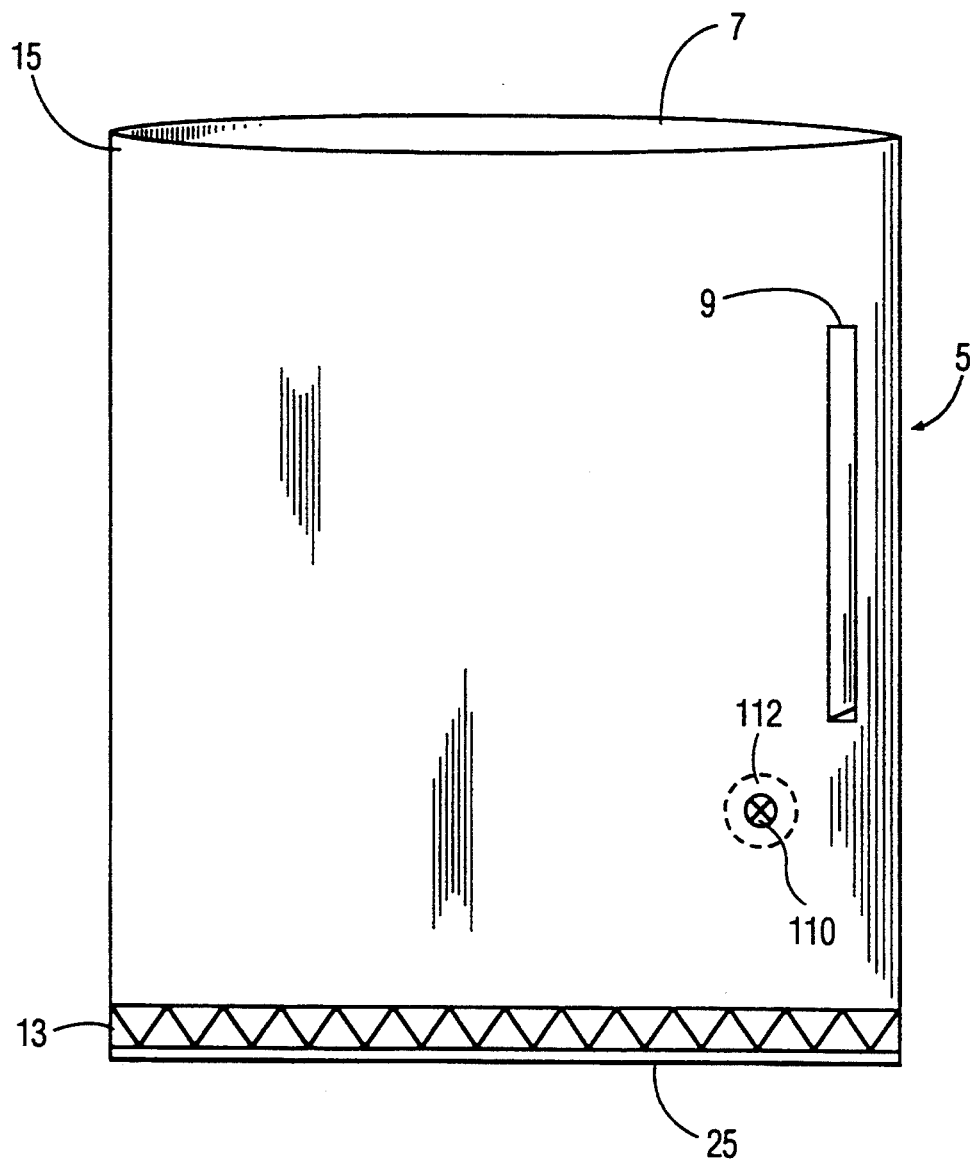
FIG. 4 is a perspective view of a third embodiment of the bag.

FIGS. 1, 3–4 illustrate the present invention which comprises a bag generally designated 5 which can consist of water-tight material such as layers polyethylene film having a top 15 and a bottom 25. At the top 15 of the bag 5 is an opening 7 for receiving the medical waste. At the bottom 25 of the bag 5 is a seal 13.

The seal 13 comprises two parallel transverse members 17 wherein each transverse member 17 is spaced apart and parallel with each other and parallel with the bottom 25 of the bag 5. Between the parallel transverse members 17 are a plurality of triangular air pockets 19 wherein each triangular pocket 19 has an apex that meets a transverse member 17. The triangular air pockets 19 have sides located at approximately 45 degrees with the transverse members 17.

Each transverse member 17 and each side of the triangular air pockets 19 can be comprised of a heat-sealed bar of the sealable material making up bag 5, such as a thermal sealable polymer material. This polyethylene material of the bag can be in the form of a tube initially. The seal 13 according to the present invention can comprise a plurality of polymer layers wherein each layer has a total thickness of at least three mils.

An adhesive tape 9 is adhesively removable from the outside of the bag 5 and can be located at a plurality of locations along the exterior of the bag 5. The tape 9 can be peeled away from the bag 5 and used to seal the disposable waste within the bag 5.

A normally-closed valve 110 is located at any one of a plurality of locations on the bag 5 thus providing access for a central vacuum system of a medical facility to the air located within the sealed bag 5.

Figure 2:
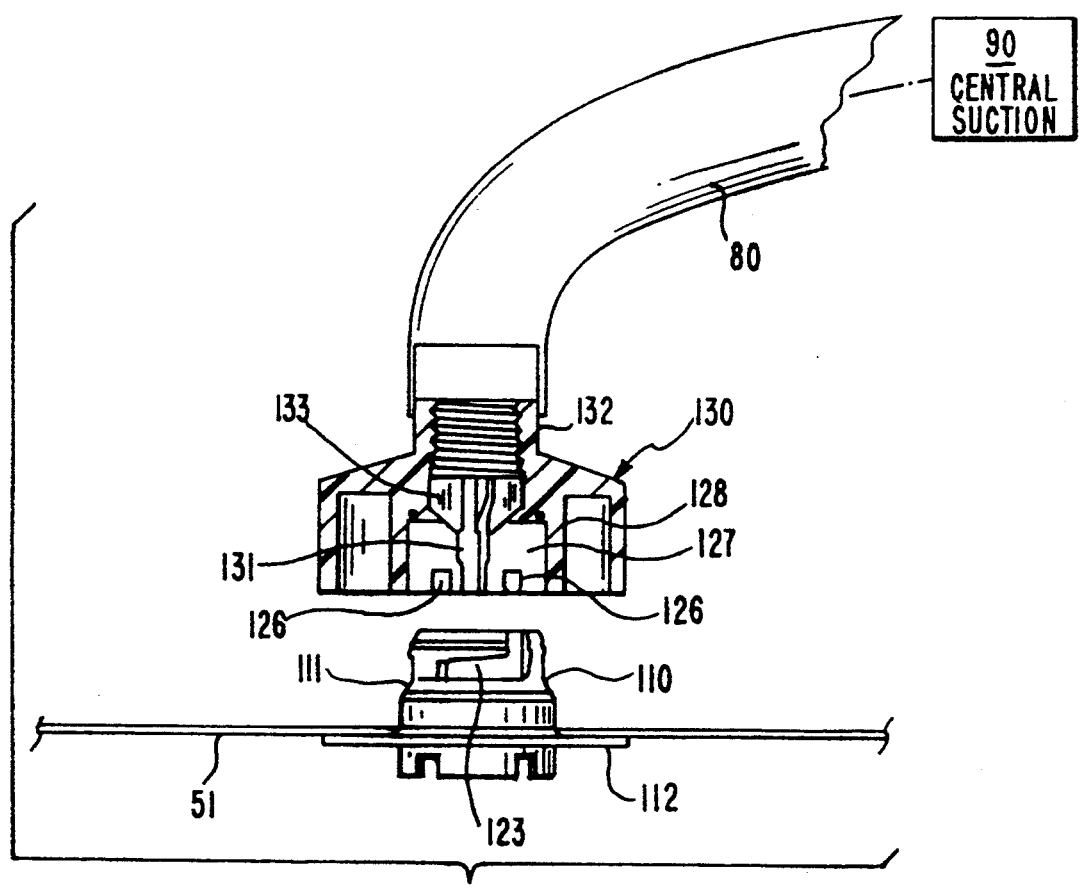
FIG. 2 is a cross-sectional view of the valve taken along line 2—2 of FIG. 1.

FIG. 2 illustrates an embodiment of the normally-closed valve 110 which is secured to the bag 5 by having a base 112 of the valve 110 adhesively or otherwise fixedly engaged with an inner side 51 of the bag 5. This valve may be of the type disclosed in U.S. Pat. No. 5,111,838 which is incorporated here by reference. The valve 110 is of a spring-loaded design which is opened when pressed by means for opening the valve, such as a coupling means or coupler 130, which is removably connected to the valve 110. The coupler 130 has a hose connector 132 for hookup with a hose 80 which leads to the central vacuum or suction 90 of a medical facility such as a hospital. The coupler 130 has an opening post 131 fixed within the coupler 130 by fins 133 defining a passage leading up through the hose connector 132 such that air can be evacuated through the open valve 110 and the hose connector 132 through the connected hose 80. The opening post 131 of the coupler 130 is of a size sufficient enough to engage the normally-closed valve 110 through a means such as a spring activating means located within the valve 110 for opening the valve 110 and gaining access to the air trapped within the bag 5. The valve 110 has a stem 111 for receiving the coupler 130. The coupler 130 has a cavity 127 circumferentially arranged around the opening post 131 within the coupler 130.

At an inner wall 128 of the coupler 130 defining the cavity 127 are located at least one projection 126 for engaging a groove 123 threaded on the stem 111 of the valve 110. The projection(s) 126 are arranged within the cavity 127 of the coupler 130 such that the projection(s) 126 are engaged in the groove 123 of the stem 111 by twisting and securing the coupler 130 therein. Once the coupler 130 is twisted onto the stem 111 of the valve 110 by engaging the projections 126 within the groove 123 of the stem 111, the opening post 131 causes the valve to be opened and access is gained to the inner side 51 of the bag 5 for sucking or vacuuming out excess air through the hose 80 to the central vacuum system 90. See U.S. Pat. No. 5,111,838 for additional details on the construction and operation of the valve.

As illustrated in FIGS. 1, 3–4, the valve 110 can be located at any location on the bag 5. The preferred location is shown in FIG. 1, however, with the valve centrally located.

Figure 5:
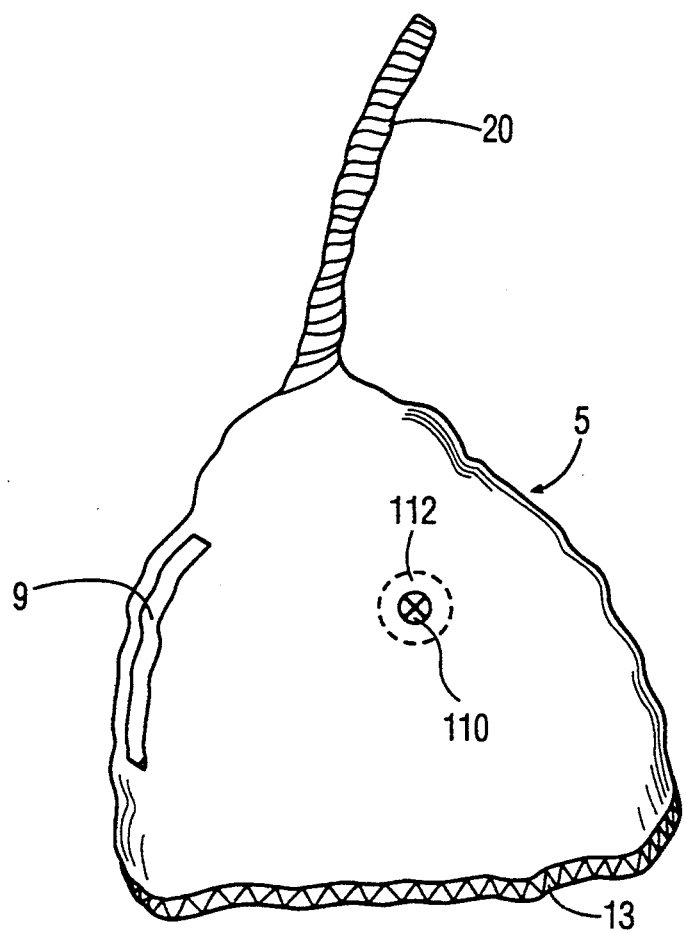
FIG. 5 is a perspective view of the bag after being filled with waste and sealed at the top by twisting.
Figure 6:
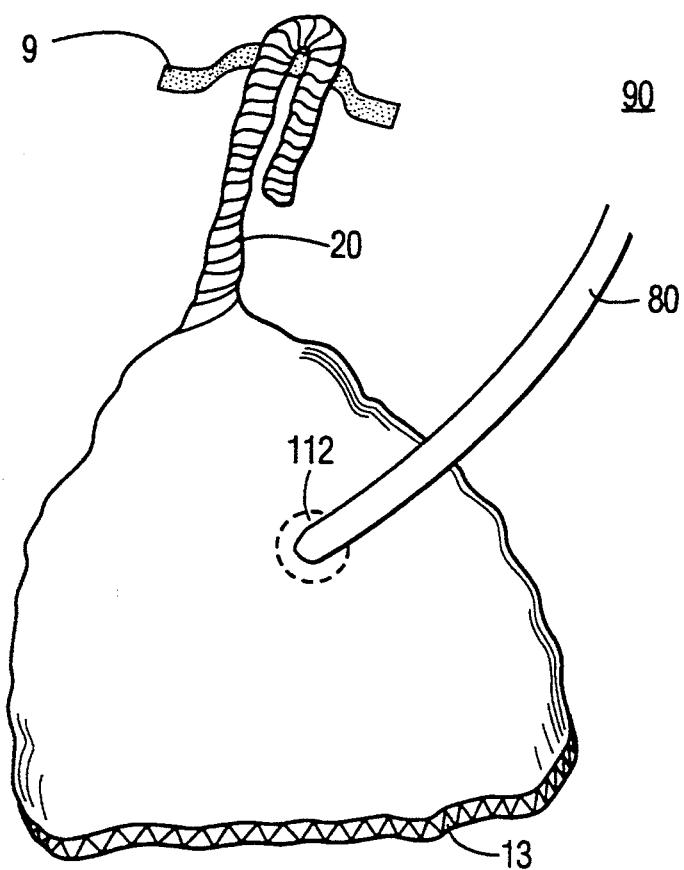
FIG. 6 is a perspective view of the bag illustrating the final sealing of the bag and accompanying hookup to the central vacuum system.
Figure 7:
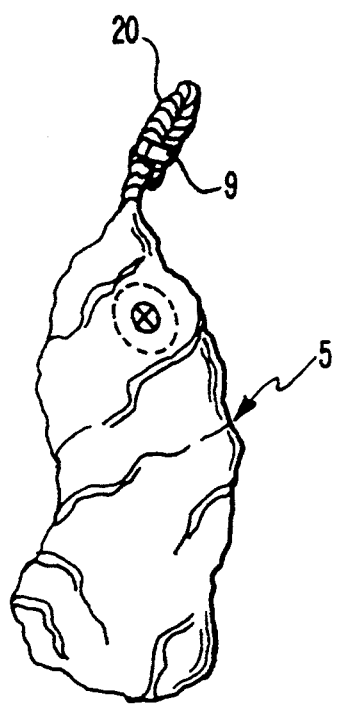
FIG. 7 is a perspective view of the bag after excess air is sucked out of the bag by the central vacuum system.

FIG. 5 illustrates that once the bag 5 is filled with medical waste, the top 15 of the bag 5 near the opening 7 can be closed by twisting for sealing the bag by forming a twist 20 which is in the form of a twisted extension extending from the bag 5. In order for the bag 5 to be properly sealed, the twist 20 is bent onto itself and the tape 9 is removed from the bag 5 and wrapped around the twist 20 thereby binding the twist 20 to itself, as illustrated in FIGS. 6 and 7. After taping the twist 20 to itself with the tape 9, the hose 80 leading from the central vacuum system 90 is connected to the coupler 130 of FIG. 2 and the coupler engaged with the normally-closed valve 110 located on the bag 5 as illustrated in FIG. 6.

FIG. 7 illustrates that after the twist 20 is taped onto itself with tape 9, the hose 80 of the central vacuum system 90 vacuums out most of the excess air contained within the bag 5 causing a substantial decrease in the volume of the bag 5 and a much smaller package of disposable medical waste.

With the present invention, it is possible to reduce the overall volume of the bag to 60% of the original volume or even less. Bags of varying sizes are also possible depending upon the needs of the medical facility involved. For example, the bag in its relatively flat configuration shown in FIG. 1, may have dimensions of 36×48", or 48×60", 24×36", 18×24", etc.

Central suction in most medical facilities can draw a vacuum of 8 to 16" of mercury and this is entirely sufficient to drastically reduce the volume of the bag from its simply sealed condition shown in FIG. 6 to its collapsed condition shown in FIG. 7.

It is also unexpectedly advantageous and effective according to the present invention, that central suction of most medical facilities not only have sufficient suction power but also are already supplied with required filters and biological safeguards since they are specifically designed for hazardous biological material. This represents a synergistic combination of the disposal bag of the invention and existing technology.

The invention is also particularly important in that hospitals must currently transport all medical waste and are precluded from incinerating such waste on site. Drastically reducing the volume of the waste thus drastically reduces transport costs. Most of the volume preexisting sealed medical waste bags was taken up by air and this is avoided by the present invention.

While a specific embodiment of the invention has been shown and described in detail to illustrate the application of the principles of the invention, it will be understood that the invention may be embodied otherwise without departing from such principles.

What is claimed is:

1. A bag for medical waste and for use in combination with a central vacuum system of a medical facility, the bag comprising:
    a body of water-tight material having an opening for receiving medical waste into an interior of the body, the opening being in an opening area of the body, the body being closed by a structure comprising a twisting of the opening area of the body near the opening to form a twist, and a bending of the twist onto itself to form a bend;
    a normally-closed valve secured to the body for releasing air entrapped within the interior of the body;
    coupling means removably engagable with the normally-closed valve for opening the valve and releasing entrapped air within the interior of the body, the coupling means adapted to be connected with a central vacuum system of a medical facility for drawing the entrapped air from the bag; and
    adhesive tape closure means detachably adhered to the surface of the body of the bag and removable for sealing the opening of the bag by adhesively wrapping the bend.

2. The bag according to claim 1 wherein the body comprises heat-sealable material.

3. The bag according to claim 2, wherein a seal is provided on the body of the bag opposite the opening for preventing leakage of the medical waste from the bag, the seal comprising a pair of straight parallel spaced apart transverse members and a plurality of angle members each extending at an acute angle between the transverse members and defining with the transverse members a plurality of triangular air-pockets extending along a seal bar, two adjacent angle members forming each pocket, and ending at one of the transverse members.

4. The bag according to claim 3, wherein the angle members each extend at an angle of about 45 degrees to the transverse members.

5. The bag according to claim 3, wherein each transverse member and each angle member comprises a heat sealed bar, the sealable material comprising thermosealable polymer material.

6. The bag according to claim 5, wherein the angle members each extend at an angle of about 45 degrees to the transverse members.

7. The bag according to claim 6, wherein the sealable material comprises a tube of polyethylene material.

8. The bag according to claim 7, wherein the body comprises a plurality of polymer layers having a thickness of at least three mils.

9. The bag according to claim 1, wherein the coupling means comprises an opening means that opens the valve allowing access into the interior of the body when the opening means engages the valve.

10. The bag according to claim 9, wherein the normally-closed valve has a stem protruding from the body of the bag for receiving the coupling means, the stem having a groove thereon for receiving and securing the coupling means.

11. The bag according to claim 10, wherein the coupling means comprises a housing having a recess circumferentially grooved within the housing for defining an inner wall, the inner wall bearing at least one projection, the recess having a width and a depth sufficient to accommodate the stem of the valve, the housing having an opening post extending through the recess and circumferentially surrounded by the inner wall, the opening post for engaging and depressing the opening means of the valve for opening the valve, the opening post having a bore therethrough for allowing air to pass through the housing, the housing being adaptably connectable to a central vacuum system for drawing entrapped air from the bag through the valve after the housing is engaged with the valve such that the recess of the housing is fitted over the stem of the valve causing the opening post to engage and depress the opening means of the valve, the housing being secured to the stem of the valve by fitting the projections of the inner wall of the housing within the groove of the stem.

12. The bag according to claim 11, wherein the body comprises a sealable material.

13. The bag according to claim 12, wherein a seal is provided on the body of the bag opposite the opening for preventing leakage of the medical waste from the bag, the seal crimping the interior of the body of the bag, the seal comprising a pair of straight parallel spaced apart transverse members and a plurality of angle members each extending at an acute angle between the transverse members and defining with the transverse members a plurality of triangular air pockets extending along a seal bar, two adjacent angle members forming each pocket, meeting only at an apex of a respective triangular pocket, and at one of the transverse members.

14. The bag according to claim 13, wherein the angle members each extend at an angle of about 45 degrees to the transverse members.

15. The bag according to claim 13, wherein each transverse member and each angle member comprises a heat sealed bar, the layers of sealable material comprising thermosealable polymer material.

16. The bag according to claim 15, wherein the angle members each extend at an angle of about 45 degrees to the transverse members.

17. The bag according to claim 16, wherein the sealable material comprises a tube of polyethylene material.

18. The bag according to claim 17, wherein the body comprises a plurality of polymer layers having a thickness of at least three mils.

* * * * *